US009326687B2

(12) United States Patent
Chu et al.

(10) Patent No.: US 9,326,687 B2
(45) Date of Patent: May 3, 2016

(54) METHODS FOR FABRICATION OF SUBSTRATES FOR SURFACE ENHANCED RAMAN SPECTROSCOPY

(71) Applicants: Wei-Kan Chu, Houston, TX (US); Dharshana N Wijesundera, Houston, TX (US); Indrajith Rajapaksa, Houston, TX (US)

(72) Inventors: Wei-Kan Chu, Houston, TX (US); Dharshana N Wijesundera, Houston, TX (US); Indrajith Rajapaksa, Houston, TX (US)

(*) Notice: Subject to any disclaimer, the term of this patent is extended or adjusted under 35 U.S.C. 154(b) by 404 days.

(21) Appl. No.: 13/958,744

(22) Filed: Aug. 5, 2013

(65) Prior Publication Data

US 2014/0081150 A1 Mar. 20, 2014

Related U.S. Application Data

(60) Provisional application No. 61/679,718, filed on Aug. 4, 2012, provisional application No. 61/679,767, filed on Aug. 5, 2012.

(51) Int. Cl.
*A61B 5/00* (2006.01)
*G01N 21/65* (2006.01)

(52) U.S. Cl.
CPC ............ *A61B 5/0075* (2013.01); *G01N 21/658* (2013.01)

(58) Field of Classification Search
CPC ............................ A61B 5/0075; G01N 21/658
See application file for complete search history.

(56) References Cited

U.S. PATENT DOCUMENTS

| 6,699,724 B1 | 3/2004 | West et al. |
| 2010/0245814 A1 | 9/2010 | Jablonski et al. |
| 2011/0026019 A1 | 2/2011 | Tyagi et al. |

FOREIGN PATENT DOCUMENTS

| EP | 1511980 | 9/2007 |
| WO | 2012-026882 A1 | 3/2012 |

OTHER PUBLICATIONS

PCT ISR.

*Primary Examiner* — Mark Remaly
(74) *Attorney, Agent, or Firm* — Robert W Strozier

(57) ABSTRACT

Methods for fabricating metal nano-particle embedded enhancement substrates used for surface enhanced Raman spectroscopy (SERS) including ion implanting metal nano-particles into the substrate and etching the substrate to partially expose the metal nano-particles. The resulting material is useful as a SERS substrate for detection of molecules adsorbed on it by surface enhanced Raman spectroscopy.

25 Claims, 4 Drawing Sheets

METHODS FOR FABRICATION OF SUBSTRATES FOR SURFACE ENHANCED RAMAN SPECTROSCOPY

RELATED APPLICATIONS

This application claims the benefit of and priority of U.S. Provisional Patent Application Ser. Nos. 61/679,718 filed Aug. 4, 2012 (4 Aug. 2012) and 61/679,767 filed Aug. 5, 2012 (5 Aug. 2012).

BACKGROUND OF THE INVENTION

1. Field of the Invention

Embodiments of the present invention relates to methods for fabricating metal nano-particle embedded enhancement substrates used for surface enhanced Raman spectroscopy (SERS) and surfaces for SERS.

More particularly, the present invention relates to methods for fabricating metal nano-particle embedded enhancement substrates used for surface enhanced Raman spectroscopy (SERS) and surfaces for SERS, where the methods include ion implanting an initial substrate (matrix) with metal ions up to a dose and at a beam current density sufficient to form metal nano-particles in the matrix with or without subsequent thermal annealing and optionally etching of the implanted surface to partially expose the metal nano-particles to form a SERS substrate.

2. Description of the Related Art

Surface enhanced Raman spectroscopy (SERS) is used for detection and identification of molecules present in minute quantities. The molecule being detected is adsorbed on a substrate consisting of nano-sized metal features, which is known to enhance the Raman scattering signal from the adsorbed molecule by many orders of magnitude. The large signal enhancement facilitates the detection of molecules present in very small quantities and the high sensitivity is beneficial in detection of chemicals in trace quantities, in bio medical applications, for example, in detection of pathogens or identification of tissue anomalies indicative of medical conditions.

To date, methods for preparation of SERS substrates have shortcomings with reproducibility of SERS detection. Advanced nano-structured substrates that render reproducible results require complex fabrication techniques having many fabrication steps thereby have a high production cost. Further, such substrates have a limited shelf life. The existing fabrication techniques have less flexibility with regard to the choice of initial substrate (matrix) and the geometry of the matrix. For example, a fabrication method that is applicable on a plane, wafer-shaped starting substrate may not be equally applicable to a probe shaped initial substrate, such as the surface of an optical fiber. Existing fabrication techniques that yield high performance may not be applicable to different materials that make up the initial substrate. For example, a method used for nano-structure fabrication on silicon may not be suited for fabrication on glass.

Since the discovery of surface enhanced Raman spectroscopy (SERS), there have been many reported methods for fabrication of substrates that show SERS effect. Certain methods of fabricating SERS substrates rely on making metallic structures with sizes and separations far less than the wavelength of excitation light source to induce high electromagnetic field enhancements. Some of the present techniques include directed patterning approach using nano-sphere lithography and E-beam lithography where patterns are produced on a substrate, typically using Ag or Au. Ag has been found to be the best material for surface enhancement. The challenge in these techniques is to reduce the distance between features due to the limitations of the lithographic techniques. Another approach utilizes random features arising, for example, from electro deposition and sputter coating. However, due to the limitations of the inherent process parameters, the controllability and reproducibility of these techniques are poor. Here, we show a technique where high dose Ag ion implantation into silicon is utilized to produce an Ag nano particle-Si composite, which is an effective, stable and reproducible SERS substrate.

Thus, there is a need in the art for SERS substrate manufacturing technique that addresses the problems with prior art manufacturing techniques, where high dose metal ion implantation into substrate is utilized to produce a metal nano-particle/substrate composite, which is an effective, stable, and reproducible SERS substrate.

SUMMARY OF THE INVENTION

Embodiments of this invention provide methods for fabricating nano-structured substrates for surface enhanced Raman spectroscopy (SERS) that overcomes the shortcomings described above.

Embodiments of this invention provide SERS substrates or SERS probes, such as fiber optic SERS probes, fabricated employing the method described herewith. In certain embodiments, the nano particles embedded in the substrate surface includes particles having a largest diameter ranging between about 0.01 nm and about 200 nm; having shapes that are spherical or near spherical in shape, where near spherical in shape means that the shape may be ellipsoidal or a distorted spherical shape (e.g., flatted on at the poles, squeezed at the equator, or other distorted spherical shapes), and having an inter-particle separation of less than 50 nm. In other embodiments, the nano particles embedded in the substrate surface includes particles having a largest diameter ranging between about 0.1 nm and about 100 nm; having shapes that are spherical or near spherical in shape, where near spherical in shape means that the shape may be ellipsoidal or a distorted spherical shape (e.g., flatted on at the poles, squeezed at the equator, or other distorted spherical shapes), and having an inter-particle separation of less than 40 nm. In other embodiments, the nano particles embedded in the substrate surface includes particles having a largest diameter ranging between about 0.1 nm and about 50 nm; having shapes that are spherical or near spherical in shape, where near spherical in shape means that the shape may be ellipsoidal or a distorted spherical shape (e.g., flatted on at the poles, squeezed at the equator, or other distorted spherical shapes), and having an inter-particle separation of less than 30 nm. In other embodiments, the nano particles embedded in the substrate surface includes particles having a largest diameter ranging between about 0.1 nm and about 20 nm; having shapes that are spherical or near spherical in shape, where near spherical in shape means that the shape may be ellipsoidal or a distorted spherical shape (e.g., flatted on at the poles, squeezed at the equator, or other distorted spherical shapes), and having an inter-particle separation of less than 20 nm. In other embodiments, the nano particles embedded in the substrate surface includes particles having a largest diameter ranging between about 0.1 nm and about 10 nm; having shapes that are spherical or near spherical in shape, where near spherical in shape means that the shape may be ellipsoidal or a distorted spherical shape (e.g., flatted on at the poles, squeezed at the equator, or other distorted spherical shapes), and having an inter-particle separation of less than 20 nm. In other embodiments, the nano particles embedded in the substrate surface includes particles having a largest diameter ranging between about 0.5 nm and about 10 nm; having shapes that are spherical or near spherical in shape, where near spherical in shape means that the shape may be ellipsoidal or a distorted spherical shape (e.g., flatted on at the poles, squeezed at the equator, or other distorted spherical shapes), and having an inter-particle separation of less than 10 nm. In other embodiments, the nano particles embedded in the substrate surface includes particles having a largest diameter ranging between about 0.5 nm and about 10 nm; having shapes that are spherical or near spherical in shape, where near spherical in shape means that the shape may be ellipsoidal or a distorted spherical shape (e.g., flatted on at the poles, squeezed at the equator, or other distorted spherical shapes), and having an inter-particle separation of less than 5 nm. In other embodiments, the nano particles embedded in the substrate surface includes particles having a largest diameter ranging between about 1.0 nm and about 10 nm; having shapes that are spherical or near spherical in shape, where near spherical in shape means that the shape may be ellipsoidal or a distorted spherical shape (e.g., flatted on at the poles, squeezed at the equator, or other distorted spherical shapes), and having an inter-particle separation of less than 2 nm. In other embodiments, the nano particles embedded in the substrate surface includes particles having a size ranging between about 0.5 nm and about 50 nm; having shapes that are spherical or near spherical in shape, where near spherical in shape means that the shape may be ellipsoidal or a distorted spherical shape (e.g., flatted on at the poles, squeezed at the equator, or other distorted spherical shapes), and having a inter-particle separation between 0 nm and 50 nm. In other embodiments, the nano particles embedded in the substrate surface includes particles having a size ranging between about 0.5 nm and about 25 nm; having shapes that are spherical or near spherical in shape, where near spherical in shape means that the shape may be ellipsoidal or a distorted spherical shape (e.g., flatted on at the poles, squeezed at the equator, or other distorted spherical shapes), and having a inter-particle separation between 0 nm and 25 nm. In other embodiments, the nano embedded in the substrate surface includes particles having a size ranging between about 0.5 nm and about 10 nm; having shapes that are spherical or near spherical in shape, where near spherical in shape means that the shape may be ellipsoidal or a distorted spherical shape (e.g., flatted on at the poles, squeezed at the equator, or other distorted spherical shapes), and having a inter-particle separation between 0 nm and 10 nm. In other embodiments, the nano particles embedded in the substrate surface includes particles having a size ranging between about 1.0 nm and about 10 nm; having shapes that are spherical or near spherical in shape, where near spherical in shape means that the shape may be ellipsoidal or a distorted spherical shape (e.g., flatted on at the poles, squeezed at the equator, or other distorted spherical shapes), and having a inter-particle separation between 0 nm and 5 nm. In other embodiments, the nano particles embedded in the substrate surface includes particles having a size ranging between about 1.0 nm and about 10 nm; having shapes that are spherical or near spherical in shape, where near spherical in shape means that the shape may be ellipsoidal or a distorted spherical shape (e.g., flatted on at the poles, squeezed at the equator, or other distorted spherical shapes), and having a inter-particle separation between 0 nm and 2 nm.

Embodiments of this invention provide methods for using the SERS substrate or probes for SERS chemical detection and biomedical detection of pathogens and anomalies in live tissue.

The SERS substrates fabricated via the methods of this invention include a semiconducting, insulating or conductive matrix or substrate embedded with metal nano-particles that are partially exposed.

Embodiments of this invention provide methods for fabricating nano-structured substrates for surface enhanced Raman spectroscopy (SERS), where first a matrix material is ion implanted with metal ions. The implantation dose is selected such that a concentration of the implanted metal exceeds a solid solubility of the metal in the matrix material. The beam current density of irradiation is chosen to trigger self-aggregation of implanted ions to form nano-particles. Alternatively, implantation may be performed at high temperature to promote self-aggregation of nano-particles. Alternatively, room temperature implantation may be used followed by a high-temperature annealing step to promote self-aggregation and nano-particle formation. The implanted surface may be cleaned to remove surface contaminants. The implanted surface of the substrate is then selectively etched to remove the surface matrix material and expose the embedded metal nano-particles either by chemical etching, electrochemical etching, ion etching, reactive ion etching, mechanical chemical polishing, and mixtures or combinations thereof. This fabrication method inherently provides a matrix that prevents clustering of nano-particles so that additional immobilization of nano-particles is unnecessary. The nano-particle size and separation can be controlled by the implantation parameters. The implantation process self assembles nano-particles subsurface; therefore the matrix inherently prevents contamination or degradation. Etching may optionally be delayed until immediately before use providing a long shelf life. The finalized substrate is then used for surface Raman enhancement.

Embodiments of this invention provide matrix materials includes a surface of a cleaved end of a fiber optic, where the fiber optic is used as a probe in SERS of a material made to be directly in contact with the end of the probe, for example, the fiber optic probe may be used for endoscopic medical diagnostics.

Embodiments of this invention provide methods for engineering substrates for surface enhanced Raman spectroscopy (SERS) by $Ag^-$ ion implantation in Si. The implantation dose and beam current density are chosen such that the Ag concentration in Si exceeds the solid solubility limit, causing aggregation of Ag and nucleating Ag nano particles. The embedded nano particles may be partially exposed by a wet etch process. Our measurements show that the so fabricated nano-composite substrates are very effective as stable and reproducible SERS substrates.

BRIEF DESCRIPTION OF THE DRAWINGS

The invention can be better understood with reference to the following detailed description together with the appended illustrative drawings in which like elements are numbered the same.

DETAILED DESCRIPTION OF THE INVENTION

Figure 1:
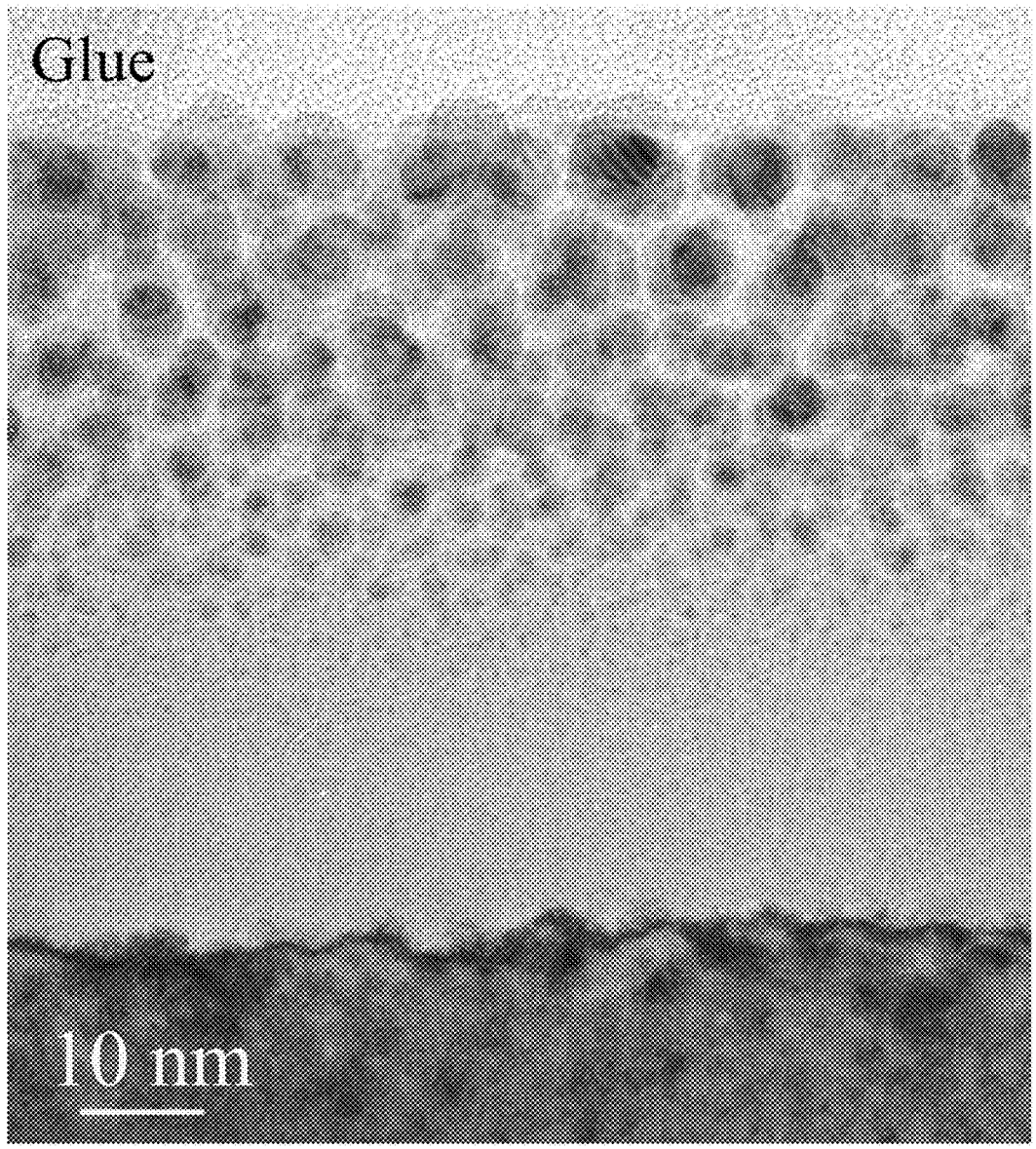
FIG. 1 depicts a cross-sectional TEM image of the $Ag^-$ negative ion implanted silicon (100) substrates before wet-etching, where implantation was carried out at an energy of 60 keV, and at a dose of $5E16/cm^2$ at a beam current density of 2.8 $\mu A/cm^2$.

The inventors have found that methods for fabrication of metal nano-particle embedded enhancement substrates used for surface enhanced Raman spectroscopy (SERS) can be implemented, where the methods permit construction of surfaces with improved properties over prior art SERS surfaces. In certain embodiments of the methods of this invention, an initial substrate (matrix) is ion implanted with metal ions up to a dose and at a beam current density where metal nano-particles are formed in the matrix with or without subsequent thermal annealing. The implanted surface of the substrate is etched to partially expose the metal nano-particles. The matrix embedded with nano-particles is then utilized as a SERS substrate for detection of molecules adsorbed on it by surface enhanced Raman spectroscopy. The matrix is not limited to a plane surface but can be the surface of a detection probe such as the surface of an optical fiber, which can be used as a probe for in-vivo medical diagnostics, for example as an endoscopic diagnostic probe.

Metal ion implantation in dielectric materials for formation of embedded nano-particles has attracted attention due to the enhanced non-linear optical properties of the so formed composite system. It has proven to be a very promising technique for the synthesis of such materials because of its intrinsic ability in controlling dopant type, concentration and space localization. Ion beam synthesis (IBS) of nano-particles may be achieved via: 1) room temperature implantation and subsequent high temperature annealing, 2) high dose room temperature implantation to exceed the threshold of spontaneous nano-particle formation, or 3) high temperature implantation. In the nano-particle fabrication processes of this invention, we employed method 2. In the high dose implantation process, implanted species migrate about and encounter other implanted ions, leading to particle nucleation and growth. During further implantation, particle growth is interrupted by ion damage, where the deposition of energetic ions fragments the particles, leading to inverse Ostwald ripening, and ultimately limiting the particle size. Due to the surface tension, the nano-clusters show well-defined spherical shape.

The present invention broadly relates to methods for fabrication of nano-structured substrates or probe surfaces for SERS. The SERS substrates fabricated via the method described consist of a semiconductor or insulating matrix, embedded with metal nano-particles that are partially exposed. Examples of the matrix material include silicon or glass wafer or the surface of the cleaved end of an optical fiber. Examples of metals include gold, silver or copper or any combination thereof. The method of the invention consists of cleaning the surface of the initial matrix material to remove any surface contaminants and native oxides that may be present. For example, a Si substrate can be cleaned via standard RCA cleaning procedure. Glass or the cleaved surface of a glass optical fiber can be cleaned with hydrofluoric acid. The matrix material is subsequently ion implanted with metal ions such as silver, gold or copper. The implantation dose is selected as for the concentration of the implanted metal exceeds the solid solubility of the metal in the matrix material. For example, a crystalline Si substrate can be implanted with 60 keV Ag negative or positive ions into a [100] polished Si wafer to a dose of $5E16/cm^2$. The beam current density of irradiation is chosen to trigger self-aggregation of implanted ions to form nano-particles, for example 2.8 $\mu A/cm^2$ for Ag in Si. The range of current density can be in a range 1 $\mu A/cm^2$ upwards to an upper limit that can be reasonably reached. Alternatively, implantation can be done at high temperature to promote self-aggregation of nano-particles. For example, for Ag in Si, the implantation can be done at 700° C. The range of annealing temperature can be from 400° C. to 1100° C. Alternatively, room temperature implantation followed by a high-temperature annealing step can be used to promote self-aggregation and nano-particle formation. For example for Ag in Si, post annealing temperature of 700° C. can be used. The post annealing temperature may range from 400° C. to 1100° C. Following implantation, the implanted surface is cleaned to remove surface contaminants. For example, the surface must be cleaned post implantation by ultraviolet-ozone to remove possible carbon surface contamination at high dose implantation.

Suitable Reagents

Substrates

Suitable substrate or matrix material include, without limitation, semiconducting substrates, insulating substrates, conductive substrates, or mixtures and combinations thereof.

Semiconducting Substrates

Suitable semiconducting substrates include, without limitation, Aluminium antimonide (AlSb) (band gap=1.6/2.2 eV); Aluminium arsenide (AlAs) (band gap=2.16 eV); Aluminium gallium arsenide (AlGaAs) (band gap=1.42-2.16 eV); Aluminium gallium arsenide nitride (AlGaAsN); Aluminium gallium arsenide phosphide (AlGaAsP); Aluminium gallium indium phosphide (AlGaInP); Aluminium gallium nitride (AlGaN) (band gap=3.44-6.28); Aluminium gallium phosphide (AlGaP) (band gap=2.26-2.45); Aluminium indium antimonide (AlInSb); Aluminium indium arsenide (AlInAs) (band gap=0.36-2.16 eV); Aluminium indium arsenide phosphide (AlInAsP); Aluminium nitride (AlN) (band gap=6.28 eV); Aluminium phosphide (AlP) (band gap=2.45 eV); Arsenic sulfide ($As_2S_3$); Barium titanate ($BaTiO_3$) (band gap=3 eV); Bismuth sulfide ($Bi_2S_3$); Bismuth telluride ($Bi_2Te_3$); Bismuth trioxide ($Bi_2O_3$); Bismuth(III) iodide ($BiI_3$); Boron arsenide ($B_{12}As_2$) (band gap=3.47 eV); Boron arsenide (BAs) (band gap=1.5 eV); Boron nitride, cubic (BN (band gap=6.36 eV); Boron nitride, hexagonal (BN (band gap=5.96 eV); Boron nitrid, nanotube (BN (band gap-5.5 eV); Boron phosphide (BP (band gap=2 eV); Cadmium antimonide ($Cd_3Sb_2$); Cadmium arsenide ($Cd_3As_2$) (band gap=0.14 eV); Cadmium manganese telluride (CdMnTe); Cadmium phosphide ($Cd_3P_2$); Cadmium selenide (CdSe) (band gap=1.74 eV); Cadmium sulfide (CdS) (band gap=2.42 eV); Cadmium telluride (CdTe) (band gap=1.49 eV); Cadmium zinc telluride (CZT CdZnTe) (band gap=1.4-2.2 eV); Chromium(III) bromide ($CrBr_3$); Copper indium gallium selenide (CIGS $Cu(In,Ga)Se_2$) (1-1.7 eV); Copper indium selenide (CIS—$CuInSe_2$) (band gap=1 eV); Copper sulfide ($Cu_2S$) (band gap=1.2 eV); Copper zinc tin sulfide (CZTS $Cu_2ZnSnS_4$) (band gap=1.49 eV); Copper(I) oxide ($Cu_2O$) (band gap=2.17 eV); Copper(II) oxide (CuO) (band gap=1.2 eV); Cuprous chloride (CuCl) (band gap=3.4 eV); Diamond (C) (band gap=5.47 eV); Europium(II) oxide (EuO); Europium(II) sulfide (EuS); Gallium antimonide (GaSb) (band gap=0.726 eV); Gallium arsenide (GaAs) (band gap=1.43 eV); Gallium arsenide antimonide (GaAsSb) (0.7-1.42 eV); Gallium arsenide antimonide nitride (GaAsSbN);

Gallium arsenide nitride (GaAsN); Gallium arsenide phosphide (GaAsP) (band gap=1.43-2.26 eV); Gallium indium arsenide antimonide phosphide (GaInAsSbP); Gallium indium nitride arsenide antimonide (GaInNAsSb); Gallium manganese arsenide (GaMnAs); Gallium nitride (GaN) (band gap=3.44 eV); Gallium phosphide (GaP) (band gap=2.26 eV); Gallium selenide (GaSe) (band gap=2.1 eV); Germanium (Ge) (band gap=0.67 eV); Indium aluminium arsenide nitride (InAlAsN); Indium antimonide (InSb) (band gap=0.17 eV); Indium arsenide (InAs) (band gap=0.36 eV); Indium arsenide antimonide (InAsSb); Indium arsenide antimonide phosphide (InAsSbP); Indium gallium antimonide (InGaSb); Indium gallium arsenide (InGaAs) (band gap=0.36-1.43 eV); Indium gallium arsenide antimonide (InGaAsSb); Indium gallium arsenide nitride (InGaAsN); Indium gallium arsenide phosphide (InGaAsP); Indium gallium nitride (InGaN) (band gap=2-3.4 eV); Indium gallium phosphide (InGaP) (band gap=1.35-2.26 eV); Indium manganese arsenide (InMnAs); Indium nitride (InN) (band gap=0.7 eV); Indium phosphide (InP) (band gap=1.35 eV); Iron disulfide ($FeS_2$) (band gap=0.95 eV); Iron(II) oxide (FeO); Lanthanum calcium manganate ($La_{0.7}Ca_{0.3}Mn_{0.3}$); Lanthanum copper oxide (La2CuO4 (band gap=2 eV); Lead manganese telluride (PbMnTe); Lead selenide (PbSe (band gap=0.27 eV); Lead telluride (PbTe (band gap=0.32 eV); Lead tin telluride (PbSnTe); Lead(II) iodide ($PbI_2$); Lead(II) sulfide (PbS) (band gap=0.37 eV); Lithium niobate ($LiNbO_3$) (band gap=4 eV); Mercury cadmium telluride (HgCdTe) (band gap=0-1.5 eV); Mercury zinc selenide (HgZnSe); Mercury zinc telluride (HgZnTe (band gap=0-2.25 eV); Mercury (II) iodide ($HgI_2$); Molybdenum disulfide ($MoS_2$); Nickel(II) oxide (NiO); Platinum silicide (PtSi); Selenium (Se) (1.74 eV); Silicon (Si) (1.11 eV); Silicon carbide (3C—SiC) (band gap=2.3 eV); Silicon carbide (4H—SiC) (band gap=3.3 eV); Silicon carbide (6H—SiC) (band gap=3.0 eV); Silicon-germanium (SiGe) (band gap=0.67-1.11 eV); Silver gallium sulfide ($AgGaS_2$); Silver sulfide ($Ag_2S$) (0.9 eV); Strontium titanate ($SrTiO_3$) (band gap=3.3 eV); Thallium germanium telluride ($Ti_2GeTe_5$); Thallium tin telluride ($Ti_2SnTe_5$); Thallium(I) bromide (TiBr); Tin dioxide ($SnO_2$) (band gap=3.7 eV); Tin sulfide (SnS) (band gap=1.0 eV); Tin sulfide ($SnS_2$) (band gap=2.2 eV); Tin sulfide (SnS); Tin telluride (SnTe); Titanium dioxide, anatase ($TiO_2$) (band gap=3.2 eV); Titanium dioxide, brookite ($TiO_2$) (band gap=2.96 eV); Titanium dioxide, rutile ($TiO_2$) (band gap=3.02 eV); Uranium dioxide ($UO_2$) (band gap=1.3 eV); Uranium trioxide ($UO_3$); Zinc antimonide ($Zn_3Sb_2$); Zinc arsenide ($Zn_3As_2$); Zinc oxide (ZnO) (band gap=3.37 eV); Zinc phosphide ($Zn_3P_2$); Zinc selenide (ZnSe) (band gap=2.7 eV); Zinc silicon phosphide ($ZnSiP_2$); Zinc sulfide (ZnS) (band gap=3.54/3.91 eV); Zinc telluride (ZnTe) (band gap=2.25 eV); and mixtures or combinations thereof.

Insulating Substrates

Suitable insulating substrates include, without limitation, glasses, silicas, aluminas, ceramics, polymers, glass reinforced polymers, or mixtures and combinations thereof.

Conductive Substrates

Suitable conductive substrates include, without limitation, metals, conductive polymers, conductive ceramics, or mixtures and combinations thereof.

Implanting Metals

Suitable metals for metal implantation of the substrates include, without limitation, any metal in the periodic table of elements. In certain embodiments, the metals include alkali metals, alkaline earth metals, transition metals, lanthanide metals, actinide metals or mixtures and combinations thereof. In other embodiments, the metals are the noble metals including ruthenium, rhodium, palladium, silver, osmium, iridium, platinum, gold or mixtures and combinations thereof. In other embodiments, the metals include copper, ruthenium, rhodium, palladium, silver, osmium, iridium, platinum, gold, or mixtures and combinations thereof. In other embodiments, the metals includes copper, silver, gold or mixtures and combinations thereof.

Ion Beam Engineering of the Substrates

In the ion beam synthesis process used herein, the substrates were prepared by implantation of 60 keV Ag negative ions into a [100] polished Si wafer to a dose of $5E16/cm^2$ at a beam current density of 2.8 ? $A/cm^2$. Fabricated composite substrates were analyzed by high resolution cross-sectional transmission electron microscopy (TEM) using a JEOL 2000FX microscope equipped with an electron dispersive spectrometer (EDS), operated at 200 kV as presented in FIG. 1. The thickness of the irradiation damaged layer of Si is 65 nm. Ag nano-particles are observed within 42 nm from the top surface. The nano-particles are generally spherical and have size distribution in the range from 10 nm near the top surface to ~1 nm. At this implantation energy of 60 keV, Ag negative ions have a projected range of 36 nm with a longitudinal straggling of 10 nm as obtained from the Stopping and Range of Ions in Matter software. Regardless, due to the considerable amount of Si substrate sputtering involved in the heavy dose implantation process, the Ag nano particle distribution is peaked toward the surface of the Si substrate, which is very favorable in fabricating SERS substrates.

At this implantation dose, a balance between silver removal due to sputtering and silver injection by implantation has already been reached, and once this equilibrium is reached, the concentration of silver in silicon cannot be further increased by increasing the implantation dose. The implantation profile in such a case ma be treated as a dynamically moving Gaussian profile, with the surface being continuously removed due to sputtering. Since the implantation dose is high, even the tail of the moving Gaussian profile well beyond the range added to straggling is sufficient to amorphize the silicon substrate. This is the reason for the observation of a Si damaged layer of nearly 65 nm although the range added to straggling is only 46 nm.

Figures 2A, 2B:
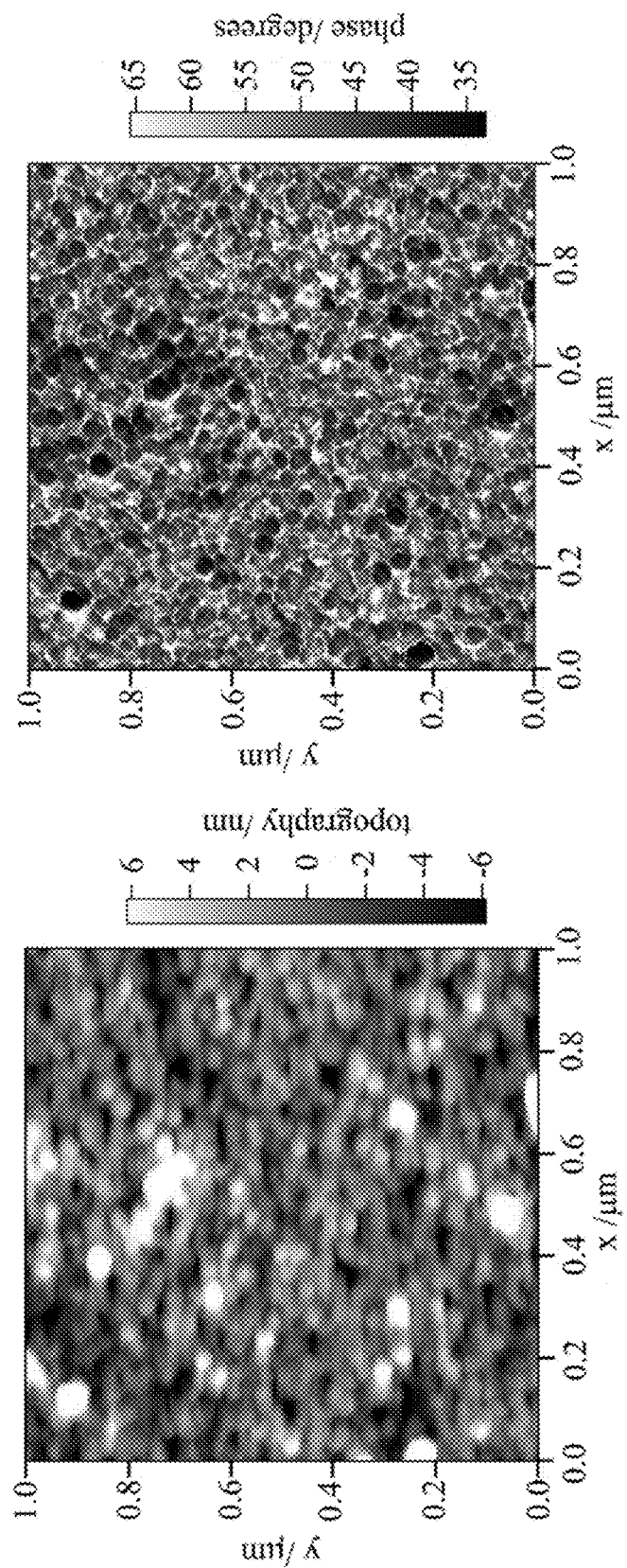
FIGS. 2A&B depicts AFM images of $Ag^-$ ion implanted Si substrates after etching with UV-ozone, hydrofluoric acid, followed by KOH, (A) topography image and (B) phase contrast image.

Upon implantation, surface Si, native Si oxide and possible organic contaminants that cover Ag nano particles prevent the substrate from being an effective SERS substrate. The substrate was therefore first cleaned in an ultraviolet-ozone cleaner for 5 min to remove any organic or carbon contamination that results in the implantation process. Next, the substrate was etched in 10% hydrofluoric acid at room temperature for 2 min to remove any native silicon oxide present on the surface. Finally, the substrate was etched in (50%) KOH at 40° C. for 10 s to etch off near surface Si and to further expose the Ag nano particles. The substrate was then rinsed with DI water. The exposure of the Ag nano particles was confirmed by an AFM in tapping mode with 3N/m stiffness, using a silicon tip of 5 nm manufacturer specified radius. FIG. 2B shows a phase contrast AFM image of the resulting surface, which separates silver in darker color and the surrounding silicon substrate in a lighter color. It shows that etching process removes silicon but leaves the silver particles intact. Since the nano particle dimensions and the tip radius are comparable, the AFM image is unable to resolve the lateral dimensions of the nano particles. The phase contrast AFM image here is therefore used to verify the exposure of Ag nano particles and should not be considered as a quantitative measure of nano particle dimensions.

An implanted dose of 5E16/cm$^2$, a beam energy of 60 keV and a beam current density 2.8 µA/cm$^2$ were chosen based on the fact that, according to our preliminary observation, these fabrication conditions are capable of producing embedded Ag nano particles in Si without requiring post implantation annealing, with particle size and separation favorable for Raman enhancement. These conditions are not optimized and they may well be improved further by changing the implantation dose, energy, current density, post implantation annealing, as well as wet etch conditions. Regardless, of possible optimization, the Raman enhancement of the substrates fabricated under the conditions of the present invention as set forth below is in an application-vice important range and shows reproducible results and are remarkable.

Surface Enhanced Raman Spectroscopy (SERS) Measurement

The substrate was immersed in a 20 mM solution of 4-methyl-benzenethiol (4-MBT, Aldrich) in ethanol for 3 hours, was washed with copious amount of ethanol and dried under a stream of dry nitrogen. The substrates were then used immediately for SERS measurement.

SERS spectra were recorded using a Renishaw in Via Raman spectrometer in backscattering geometry under 543 nm He—Ne laser excitation. The backscattered Raman signals were collected on a thermoelectrically cooled CCD detector. The accumulation time was 30 s. Laser power of 0.8 mW was focused on the sample by 20× objective with a 0.4 numerical aperture. Raman measurements were also taken on pure silicon as a control. For quantification, Raman measurement was also carried out for 0.1M 4-MBT in a 12 M NaOH solution.

We calculate the lower limit of SERS enhancement, EF, by comparing the 1076 Raman band using $EF=(I_{SERS}/N_{SERS})/(I_{norm}/N_{norm})$, where $I_{norm}$ is Raman intensity for the normalization reference sample (0.1M 4-MBT in 12M NaOH), $N_{norm}$ is the number of molecules in the focal volume (0.3 pL) of the Raman system, and $I_{SERS}$ and $N_{SERS}$ are the same for the 4-MBT adsorbed nano silver substrate. We assumed 100% surface coverage of a mono layer of 4-MBT in the focal spot area to find the lower limit of the Raman enhancement factor.

Ion Metal Implantation

The implanted surface of the substrate is then selectively etched to partially expose the embedded metal nano-particles either by chemical or electrochemical reaction, ion etching, reactive ion etching, mechanical chemical polishing, or combinations of these etching methodologies. For example, for 60 KeV, 2.8 µA/cm$^2$ Ag implanted in Si, the substrate is etched with 10% HF for 2 minutes followed by a (50%) KOH etch at 40 C for 10 seconds, followed by a DI water rinse. FIG. 2B shows a phase contrast AFM image of the surface of the etched, exposed Ag nano-particles on the substrate. In case of a glass or glass optical fiber, hydrofluoric acid etch may be used for this step.

Figure 3A:
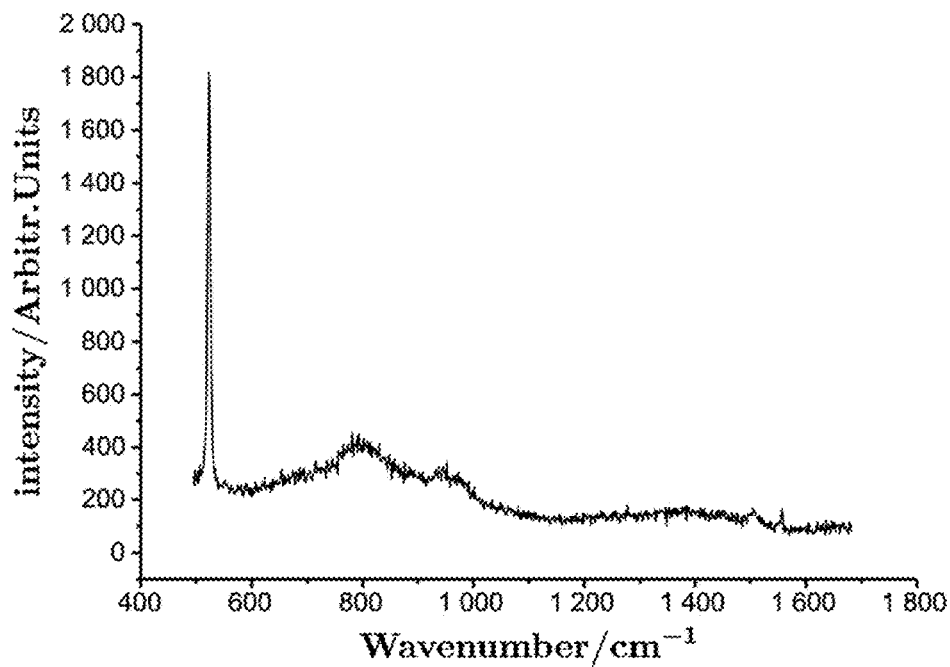
FIGS. 3A&B depict SERS spectra of 4-MBT adsorbed on nano silver Si substrates: (A) on un-implanted Si (control) region and (B) in the Ag ion implanted region.
Figure 3B:
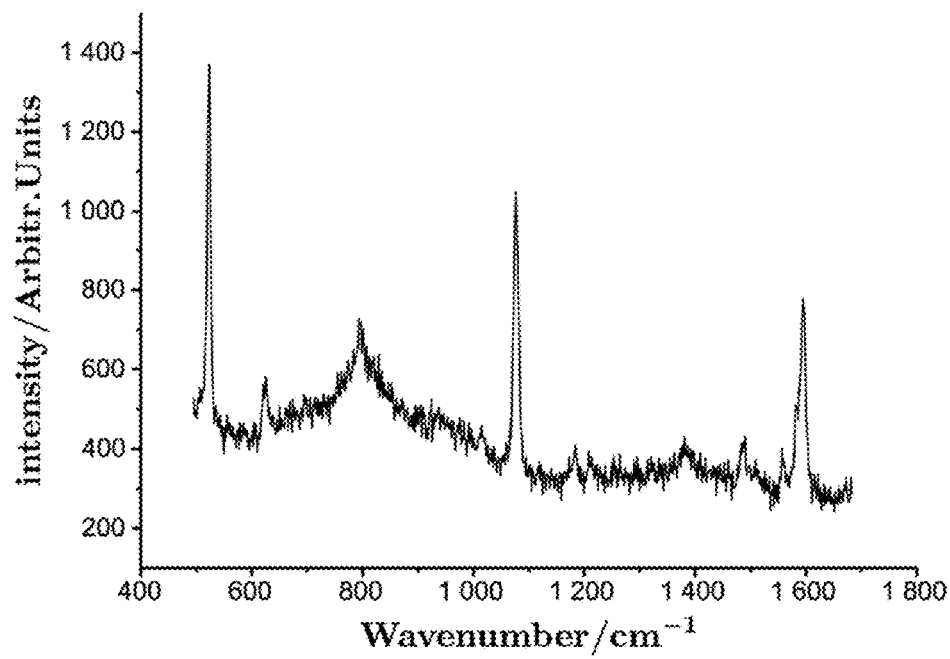

The fabricated substrate or fiber optic probe is then utilized as the enhancing substrate in SERS. FIGS. 3A&B show SERS measurements of 4-methyl-benzenethiol (4-MBT) using a Ag implanted Si substrate for Raman enhancement. The excitation source in this example is a 543 nm He—Ne laser. FIG. 3A shows the outcome for the un-implanted (control) region, and FIG. 3B shows the outcome in the implanted region. Bands at 1076 cm$^{-1}$ and 1594 cm$^{-1}$ are not seen in the control (un-implanted) sample. The calculated minimum SERS enhancement factor for this example is 2.0E5. This value represents the lower limit and the actual value would be higher.

The fabrication technique described herewith can produce highly effective, stable, and reproducible SERS substrates or SERS probes. The fabrication cost is comparatively lower and includes standard procedures and equipment used in semiconductor industry. The shelf life of un-etched substrates is at least up-to 4 years according to test results of the example discussed. The simple and rapid etching step with HF and KOH (for Si or glass matrix) and can be done at the user end producing a fresh substrate immediately before use. The fabrication method described herewith is flexibly applicable to wide variety of matrix materials of different geometries other that a planar surface, for example, fiber optic detection probes.

Discussion

The Ag implanted area shows SERS as shown in FIG. 3B of 4-MBT bands at 1076 cm$^1$ and 1594 cm$^{-1}$, which is not observed in the control (un-implanted) sample as shown in FIG. 3A. The calculated minimum SERS enhancement factor is 2.0E5. This value represents the lower limit, and the actual value would be higher.

Figures 4A, 4B:
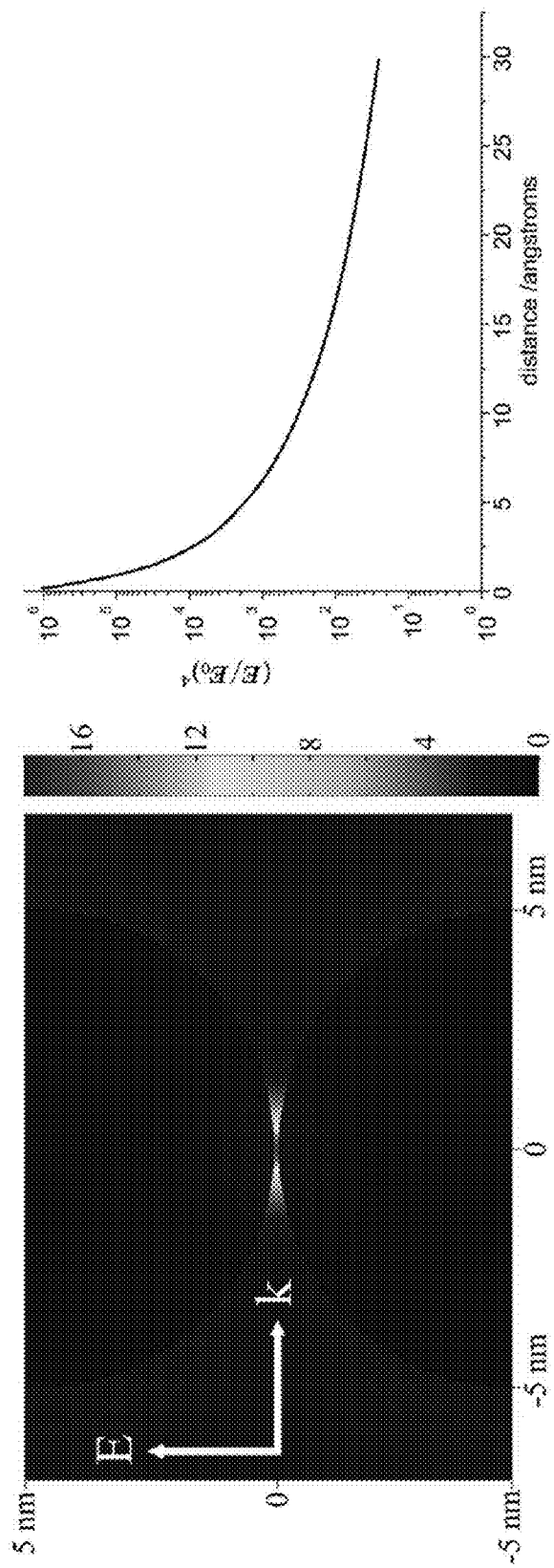
FIGS. 4A&B depict simulations of scattered electric field intensity between two Ag nano particles each 10 nm in diameter: (A) distribution of field enhancement, and (B) electric field enhancement versus distance between particles.

Surface Raman enhancement has been attributed to both chemical and electromagnetic enhancement factors. We believe our Ag nano-particle geometry is effective for electromagnetic field enhancement driven by surface plasmons. To better understand the electromagnetic Raman signal enhancement, we have also simulated a two Ag nano-particle system in 2D via finite-element method with COMSOL. The electromagnetic radiation is modeled as a plane wave. The simulation domain was a 2 µm diameter circular region with perfectly matched layer (PML) thickness of 500 nm. We consider silver nano-particles of 10 nm diameter in modeling. Due to multi reflections of the PML, we did not model the silicon substrate as this would include numerical error, and the present 2D model is used for qualitative analysis only. FIG. 4A shows the field enhancement for two adjacent Ag particles. Our model shows high electric field enhancement between Ag nano-particles. This region is the well-known "hot spot region" and is the cause of the high SERS electromagnetic enhancement. We further simulated the dependence of the field enhancement on the distance between two Ag nano-particles as shown in FIG. 4B. The surface enhancement factor shows a rapid increase as the distance between the particles decreased. The distribution of Ag nano particles and the spacing in between them as visible in the TEM image as shown in FIG. 1 and the corresponding AFM phase image as shown in FIG. 2B indicates that Ag negative ion implanted substrates should have a high number of hotspot areas. The TEM images show that these Ag particles have a separation of 0 nm to 2 nm that is ideal for SERS enhancement, which accounts for the high SERS enhancement that we observe.

CONCLUSION

In conclusion, we have demonstrated a fabrication process of SERS substrates via Ag ion implantation in silicon. We show that our Ag nano-particle substrates have an optimized geometry for SERS enhancement in terms of nano-particle and size and separation. The fabrication process gives highly reproducible outcome; the technique is cost effective and straightforward, requiring only a small number of processing steps.

CLOSING

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

We claim:

1. A method for fabricating substrates for surface enhanced Raman spectroscopy (SERS) comprising the steps of:
    implanting negatively or positively charged metal ions into a matrix material, and
    growing near-surface or subsurface metal nano-particles within the matrix material.

2. The method of claim 1, further comprising the step of:
    prior to the growing step, thermal annealing the implanted matrix.

3. The method of claim 1, further comprising the step of:
    subsequently to the growing step, selective surface etching the surface of the matrix to expose or partially expose the metal nano-particles.

4. The method of claim 3, wherein the etching is selected from the group consisting of chemical etching, electrochemical etching, ion etching, reactive ion etching, mechanical chemical polishing, and mixtures or combinations thereof.

5. The method of claim 1, wherein the implanting metal is selected from the group consisting of metals from the periodic table of elements including alkali metals, alkaline earth metals, transition metals, lanthanide metals, actinide metals or mixtures and combinations thereof.

6. The method of claim 1, wherein the implanting metal is selected from the group consisting of ruthenium, rhodium, palladium, silver, osmium, iridium, platinum, gold, and mixtures or combinations thereof.

7. The method of claim 1, wherein the implanting metal is selected from the group consisting of copper, ruthenium, rhodium, palladium, silver, osmium, iridium, platinum, gold, and mixtures or combinations thereof.

8. The method of claim 1, wherein the implanting metal is selected from the group consisting of silver, gold, copper, and mixtures or combinations thereof.

9. The method of claim 1, wherein the matrix material is selected from the group consisting of a semiconducting material, an insulating material, a conducting substrate, mixtures or combinations thereof.

10. The method of claim 9, wherein the insulating material is a surface of a tip of an optical fiber.

11. The method of claim 1, wherein the implanting dose of the metal in the matrix material exceeds the solubility limit of the metal in the matrix material.

12. The method of claim 1, wherein the implanting step is carried out at room temperature or at an elevated temperature.

13. The method of claim 1, wherein the implanting beam current density is sufficient to trigger growth of metal nano-particles without post implantation high-temperature annealing.

14. The method of claim 1, wherein the nano particles ion implanted in the substrate surface includes particles having a largest diameter ranging between about 0.01 nm and about 200 nm; having shapes that are spherical or near spherical in shape, and having an inter-particle separation of less than 50 nm.

15. The method of claim 1, wherein the nano particles ion implanted in the substrate surface includes particles having a largest diameter ranging between about 1.0 nm and about 10 nm; having shapes that are spherical or near spherical in shape, and having an inter-particle separation of less than 2 nm.

16. A method for using an surface enhanced Raman spectroscopy substrates comprising:
    obtaining an optical fiber including a surface having a plurality of metal nanoparticles formed therein, where the metal nanoparticles are ion implanted into the surface of the matrix material as negative metal ion at a concentration sufficient to form the nanoparticles in the surface of the matrix material, and
    endoscopically inserting the optical fiber into a human or animal including mammals, and
    performing in-vivo surface enhanced Raman spectroscopic diagnostics.

17. The method of claim 16, wherein the implanting metal is selected from the group consisting of metals from the periodic table of elements including alkali metals, alkaline earth metals, transition metals, lanthanide metals, actinide metals or mixtures and combinations thereof, wherein the matrix material is selected from the group consisting of a semiconducting material, an insulating material, a conducting substrate, and mixtures or combinations thereof.

18. The method of claim 16, wherein the nano particles ion implanted in the substrate surface includes particles having a largest diameter ranging between about 0.01 nm and about 200 nm; having shapes that are spherical or near spherical in shape, and having an inter-particle separation of less than 50 nm.

19. The method of claim 16, wherein, the nano particles ion implanted in the substrate surface includes particles having a largest diameter ranging between about 0.1 nm and about 20 nm; having shapes that are spherical or near spherical in shape, and having an inter-particle separation of less than 20 nm.

20. The method of claim 16, wherein the nano particles ion implanted in the substrate surface includes particles having a largest diameter ranging between about 1.0 nm and about 10 nm; having shapes that are spherical or near spherical in shape, and having an inter-particle separation of less than 2 nm.

21. A surface enhanced Raman spectroscopy (SERS) substrate comprising:
    a matrix material including a surface having a plurality of metal nanoparticles formed therein, where the metal nanoparticles are ion implanted into the surface of the matrix material as negative metal ion at a concentration sufficient to form the nanoparticles in the surface of the matrix material.

22. The substrate of claim 21, wherein the implanting metal is selected from the group consisting of metals from the periodic table of elements including alkali metals, alkaline earth metals, transition metals, lanthanide metals, actinide metals or mixtures and combinations thereof, wherein the matrix material is selected from the group consisting of a semiconducting material, an insulating material, a conducting substrate, and mixtures or combinations thereof.

23. The substrate of claim 21, wherein the nano particles ion implanted in the substrate surface includes particles having a largest diameter ranging between about 0.01 nm and about 200 nm; having shapes that are spherical or near spherical in shape, and having an inter-particle separation of less than 50 nm.

24. The substrate of claim 21, wherein the nano particles ion implanted in the substrate surface includes particles having a largest diameter ranging between about 0.1 nm and about 20 nm; having shapes that are spherical or near spherical in shape, and having an inter-particle separation of less than 20 nm.

25. The substrate of claim 21, wherein the nano particles ion implanted in the substrate surface includes particles having a largest diameter ranging between about 1.0 nm and about 10 nm; having shapes that are spherical or near spherical in shape, and having an inter-particle separation of less than 2 nm.

\* \* \* \* \*